United States Patent
Pietikainen et al.

[11] Patent Number: 6,157,698
[45] Date of Patent: Dec. 5, 2000

[54] METHOD FOR ANALYZING CHARACTERISTICS OF A MOVING OBJECT, SUCH AS A LOG

[75] Inventors: Markku Pietikainen; Heikki Ailisto, both of Oulu, Finland

[73] Assignee: Bintec Oy, Hollola, Finland

[21] Appl. No.: 09/125,623

[22] PCT Filed: Feb. 27, 1997

[86] PCT No.: PCT/FI97/00132

§ 371 Date: Oct. 30, 1998

§ 102(e) Date: Oct. 30, 1998

[87] PCT Pub. No.: WO97/32199

PCT Pub. Date: Sep. 4, 1997

[30] Foreign Application Priority Data

Feb. 27, 1996 [FI] Finland .................................. 960914

[51] Int. Cl.[7] .................................................. G01B 15/06
[52] U.S. Cl. ................................ 378/58; 378/23; 378/24; 378/27; 702/38
[58] Field of Search .................................. 378/58, 62, 23, 378/24, 27; 702/38

[56] References Cited

U.S. PATENT DOCUMENTS 5,023,805  6/1991  Aune et al. .
5,394,342  2/1995  Poon .

FOREIGN PATENT DOCUMENTS 0701116   3/1996  European Pat. Off. .
WO9105245  4/1991  WIPO .
WO9419681  9/1994  WIPO .

*Primary Examiner*—David V. Bruce
*Assistant Examiner*—Pamela R. Hobden

[57] ABSTRACT

A method for determining the properties of a log, in which a moving log is radiographed by at least more than one X-radiation source, and the radiographic information is received by a detector array measuring radiation. Stemwood and knots of the log are calculated by a principle which is based on a known geometry and density of stemwood and knots. After measurement, the effect of stemwood in radiographic projections, and hence the analysis for locating knots, is eliminated by filtering. The knot mass is then converted from radiographic projections into volumetric elements of a cylindrical coordinate system and, from the value of each volumetric element, an evidence value representative of the presence of a knot in the element is derived. The evidence values of mutually associated elements are then combined, thus producing an aggregate evidence value which permits the knots to be located.

11 Claims, 3 Drawing Sheets

| Element (i,j) | Distance travelled by ray in element (mm) | Back projection coefficient c(h,i,j) | Projection result c(h,i,j)*p(h) |
|---|---|---|---|
| (1,2) | 8.50 | 0.12 | 1.16 |
| (2,2) | 7.50 | 0.10 | 1.02 |
| (2,3) | 4.00 | 0.05 | 0.54 |
| (3,3) | 9.50 | 0.13 | 1.29 |
| (3,4) | 11.50 | 0.16 | 1.56 |
| (11,3) | 8.50 | 0.12 | 1.16 |
| (11,4) | 11.50 | 0.16 | 1.56 |
| (12,2) | 7.00 | 0.10 | 0.95 |
| (12,3) | 5.50 | 0.07 | 0.75 |
| Total | 73.50 | 1.00 | 10.00 |

METHOD FOR ANALYZING CHARACTERISTICS OF A MOVING OBJECT, SUCH AS A LOG

This application is the national phase under 35 U.S.C. §371 of prior PCT International Application No. PCT/FI97/00132 which has an International filing date of Feb. 27, 1997 which designated the United States of America, the entire contents of which are hereby incorporated by reference.

FIELD OF THE INVENTION

The present invention relates to a procedure for determining the properties of a moving object, such as a log.

BACKGROUND OF THE INVENTION

In the related art, methods are known whereby logs are observed visually or optically in order to sort them according to their quality. In a method based on visual inspection, the person performing the sorting directs the logs to different piles on the basis of visual observation. However, this method does not reveal the internal properties of the logs. In optical measurement of dimensions, the measurement is taken from the surface of the bark, which means that variations in bark thickness may result in considerable errors in the determination of the dimensions and volume of the log. These methods for the inspection of logs are mainly focused on measuring log thickness, and the measurement data is communicated to a sorter, who directs the logs manually to appropriate piles according to this information. These methods generally provide no other information about the logs. According to investigations, another drawback is that when the sorting is done by a human sorter, only about half of the logs are sorted fairly correctly with regard to the desired result.

A further drawback with the above methods is that, even if metal detectors are used, it is not possible to identify all foreign objects, such as rocks and non-ferrous metals, that may be present in the logs. Therefore, such objects remain inside the log and may cause damage in the equipment used for further processing of the logs. Finnish patent application no. FI893938 (corresponding to U.S. Pat. No. 5,023,805) presents a method based on three-projection X-ray photography, known in itself in prior art. In this method, from each radiographic projection, the knot terminations are first determined via a longitudinal reconstruction of the log, whereupon knot vectors matching these points are calculated. The weakness of this method consists in the fact that the terminations cannot be determined sufficiently accurately and unambiguously from real logs. Among the reasons for this are overlapping knots and the moisture of fresh wood, which obliterates parts of the knot. Accordingly, what is needed is a method for determining the properties of a moving object such as a log such that the aforementioned drawbacks can be avoided or eliminated.

The object of the present invention is to eliminate the drawbacks of the methods described above and to achieve a reliable and effective method for determining the properties of logs relating to their quality. The method involves using knowledge relating to the geometry, density and other properties of the moving object, as well as inter-dependency between the properties, to allow sorting according to quality.

The operation, measuring and data processing performed by equipment of the invention is based on wood-related knowledge defined by wood quality, and on radiological application of this knowledge. The method comprises a radiological, adaptive expert system based on a knowledge of wood. The procedure can also be applied to other objects or materials moved as bulk goods.

The method has the advantage that it enables the internal defects of bulk goods moving on a conveyor line to be measured and identified using only few projections. This allows reliable determination of quality properties of logs moving at sawing speed. The measurements of the log can also be taken from the log surface beneath the bark, so that the true dimensions of the wooden part of the log can be accurately measured. Instead of using knot outlines in the pictures in a longitudinal reconstruction of the log, as in the above-mentioned patent specification, the method in accordance with the present invention employs the principles of fuzzy logic to locate, by means of a reconstruction formed in a direction perpendicular to the longitudinal axis and utilizing layered slices, three-dimensional objects in which the knot mass is concentrated.

The procedure can be used to determine internal and external properties of logs. The external properties include log length, diameter, conicity and ellipticity as well as bends, multiple crookedness, crooked-growth and volume. One of the advantages of the invention is that the diameter, conicity and volume measurements can be determined from a log with the bark on it for the log without bark. Thus, accurate measurements of the useful wood portion are obtained.

Internal defects of the log include resin pockets, rotten spots, cavities and clefts and also foreign objects, such as rocks and ferrous and other metals. The procedure provides thorough and reliable information about the knots and knot clusters as well as their quality inside the log. The procedure also reveals variations in density and moisture of the wood. By sorting the logs by quality as provided by the invention, healthy knots, dry and rotten areas and their transition zones can be determined.

An important feature regarding measurement and costs is a fast log analysis achieved at a relatively low cost. It is possible to increase both the intensity of X-ray radiation and the computing power to produce a faster analysis, but this could lead to excessive additional costs. In the accordance with an embodiment of the invention, both the intensity of X-ray radiation and the computing power are optimized and to attain the desired speed and accuracy at a relatively low cost. One of the factors contributing to this is that the amount of measurement data can be significantly reduced as compared with prior-art solutions.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DETAILED DESCRIPTION

Figure 3:
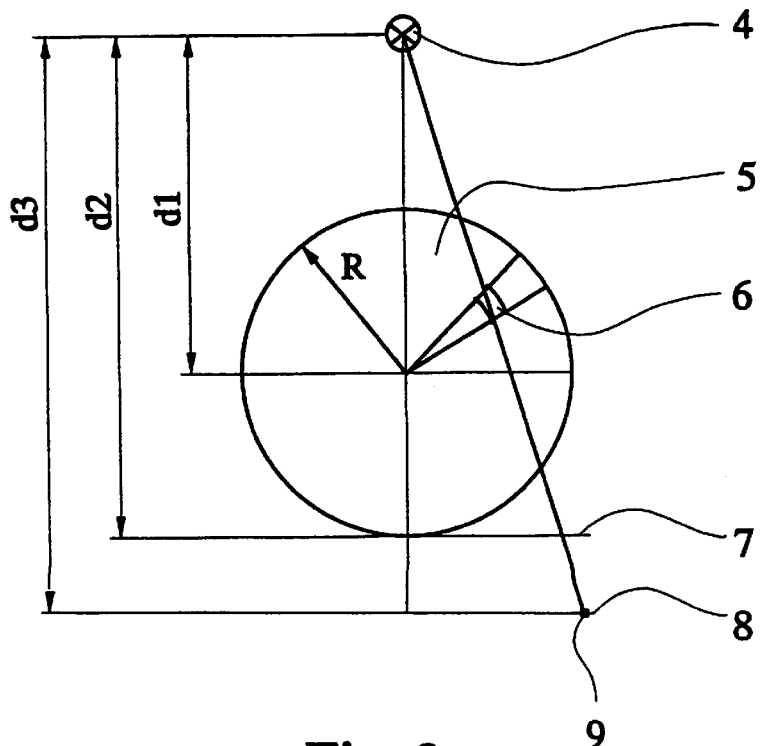
FIG. 3 illustrates the geometry of the log raying process.

The method involves the use of tomography. In medical tomography, a problem of the same type has been solved in which an object is X-rayed from many directions and the internal structure of the object is calculated from the projections. However, the number of projections can range in upwards of 500–1000. It is not possible to take as many X-rayograms of a saw log, but in practice a few, e.g. about three projections must suffice. Referring to FIG. 3, the method according to invention, a log 5 moving at sawing speed is radiographed by means of only a few, e.g. about three radiographic devices (such as X-ray apparatuses) emit a radiation capable of penetrating matter, and the picture data is stored by means of detector arrays 8, one or more detector arrays being used for each X-radiation source 4. It has been established in practice that as few as three projections are sufficient to provide enough information to allow the quality properties of a log to be measured with acceptable accuracy.

The method is not concerned with reconstructing the log from the pictures pixel for pixel as in earlier practice, but instead use is made of a knowledge of the typical geometry, density and other properties of the trunk, knots and the associated anomalies as well as the interdependencies of said properties. Typically, the pictures are analyzed to detect objects having the shape of knots or other anomalies, or parts of such objects. These are processed in a system of cylindrical coordinates which are divided into discrete volumetric elements.

The process of determining the properties of a log or a corresponding object by the method of the invention can be divided into three main parts, which will be described in greater detail below.

Part I: Preliminary processing of the measurement data is performed using the pixel-specific intensity data obtained from the radiograph in each X-raying direction, on the basis of a knowledge of wood. The analysis is based on the relative attenuation differences caused by internal objects in the log. For each wood quality, the radiological relative differences, i.e. attenuation differences, of the boundary surfaces/values between normal wood and internal objects in the wood can be defined. These relative differences are compared both in the transverse plane and in the direction of tree growth. The differences are relative from one tree to another and in the same tree depending on its moisture. These divergent areas of interest are further studied using more exact calculation methods. Thus, the measurement data relating to normal wood need not be processed further, so the processor power should be sufficient for real-time quality sorting of logs advancing at process speed. Using simple logic deduction rules, anomalies are identified as positive or negative anomalies and the boundary surface of the anomaly is determined.

Part II: Objects detected in the log are identified and their position is ascertained using the other measuring directions. The objects (knot, rotten spot, rock, etc.) are identified by making use of a wood-type specific knowledge on the basis of their location, size and relative X-ray attenuation.

Part III: Based on wood-type specific knowledge and radiographic appearance, a semi-empirical simple mathematical model or representation has been developed for objects in the wood and is applied to an object detected and identified in an area of interest, so the size and quality of the object can be determined.

Figure 1:
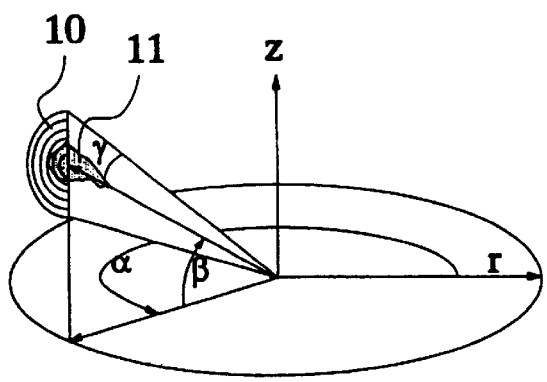
FIG. 1 illustrates a system of cylindric coordinates, as a way to describe a knot in a log.
Figure 2:
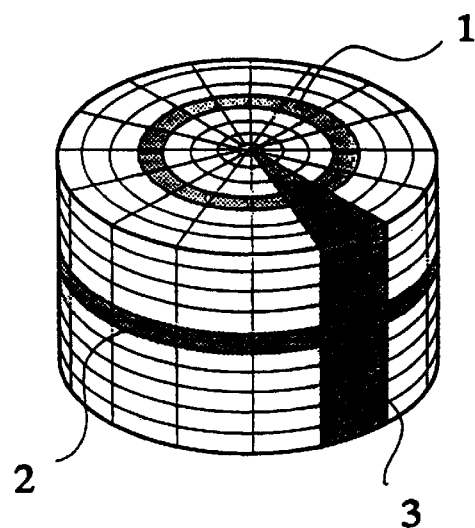
FIG. 2 shows how a log is divided into volumetric elements in cylindric coordinates.

FIG. 1 presents a system of cylindrical coordinates, consisting of an angle of rotation $\alpha$, radius r and longitudinal axis z. A slice of log trunk is a cylindrical body in which the core runs along the longitudinal axis z. Knots start at the core and grow towards the surface with an upward gradient $\beta$ and a spread angle $\gamma$. Each knot lies within a sector that contains no other knots, so each knot can be described with a conical model. A knot may contain both healthy wood 10 and rotten wood 11. As illustrated by FIG. 2, a log can be divided into circles 1, slices 2 and sectors 3, and a section comprising each of these constitutes one volumetric element, whose position is defined by the cylindrical coordinates. The slice 2 thickness along the longitudinal axis of the log represents width of the detector elements 9 of a detector array 8 in the longitudinal axis direction of the log and therefore the longitudinal log section exposed to radiography at a point in time.

FIG. 3 illustrates the geometry used in the radiological apparatus, showing only one X-ray for the sake of simplicity. When the description deals with the rays emitted by one X-radiation source 4 and the detector elements 9 receiving them, which together form a detector array 8, one radiographic projection is being referred to. Therefore, as the procedure comprises the use of three X-radiation sources and a detector array corresponding to each of these, it can be said that the measurement ultimately takes place in three radiographic projections. The X-radiation sources 4 and the corresponding detector arrays 8 are placed at an angle of 120° relative to each other and so disposed around the path of the log that the log will pass between the X-radiation sources 4 and the corresponding detector arrays 8. Thus, the X-rays emitted by the X-radiation sources penetrate the log and, depending on the properties of the log, are attenuated in different ways on their way to the detector arrays, whose detector elements 9 receive the radiation thus attenuated. Each detector array 8 consists of a series of detector elements 9 placed in a curved arrangement around the log, all of the detector elements being located at equal distances from the corresponding X-radiation source 4 and in the same plane perpendicular to the log movement as the X-radiation source. The number of radiographic projections used may be greater or smaller than three as needed.

The log 5 lies on a conveyor surface 7, where it is exposed to X-radiation from an X-radiation source 4. The radiation penetrating the log 5 is received by a detector element 9. The geometry is described by the distance d1 between the X-radiation source 4 and the center line of the log 5, the distance d2 between the X-radiation source 4 and the conveyor surface 7 and the distance d3 between the X-radiation source 4 and the detector array 8. Distance d1 depends on the log radius R as follows: d1=d2−R. The detector elements 9 of the detector array 8 are indexed each one separately. The detector element 9 receives information about a sector element 6 of the log, but also for the entire distance covered by the ray. The information consists of X-ray attenuation data.

A knot model is created by utilizing a knowledge of the typical geometry and density of knots and stemwood. Below are a few rules:
 (a) The cross-section of the trunk is roughly elliptical. The size of the cross-section can be estimated as being the mean value of the diameters of the three radiographic projections. The largest one of the diameters of the radiographic projections is used to define the circle that contains the cross-section of the reconstructed image.
 (b) All knots start from the core of the trunk. The knot is a cone which is described by an angle of rotation $\alpha$, an upward gradient β, a spread angle γ and a radial length r. The upward gradient β has certain predetermined values in degrees.

(c) All knots in a cluster of knots start from about the same point. Adjacent knots cannot lie side by side, but a minimum value has been defined for the rotational distance between knots.

(d) The density of the trunk varies from the core towards the external surface. Typical densities of sapwood, heartwood and knots have been defined experimentally.

Before the calculation, the center of the log must be brought exactly to the center of the calculation coordinates. This is done by moving the image until the log center coincides with the centre of the coordinates. The log center again is obtained by determining the edges of the log from the radiographic projection by thresholding and then calculating the log diameter from the edge data obtained.

An X-ray penetrating a log undergoes greater attenuation when passing through a knot than when passing through other, softer wood material. By examining the rays received by the detector elements 9, it is possible to obtain hints, which at this stage constitute unreliable individual pieces of information, indicating that the samples represented by certain pixel groups or detector element groups might contain knot mass. By combining the images and hints indicating the presence of knots from all radiographic projections, a certain truth value is obtained for the volumetric element. By combining the truth values of adjacent volumetric elements, a truth value is obtained for the assumption that the sector is part of a knot. The truth values are assigned values in the range −1−+1. The values −1, 0 and +1 may be defined verbally as meaning "absolutely no", "undefined" and "absolutely yes".

Figure 4:
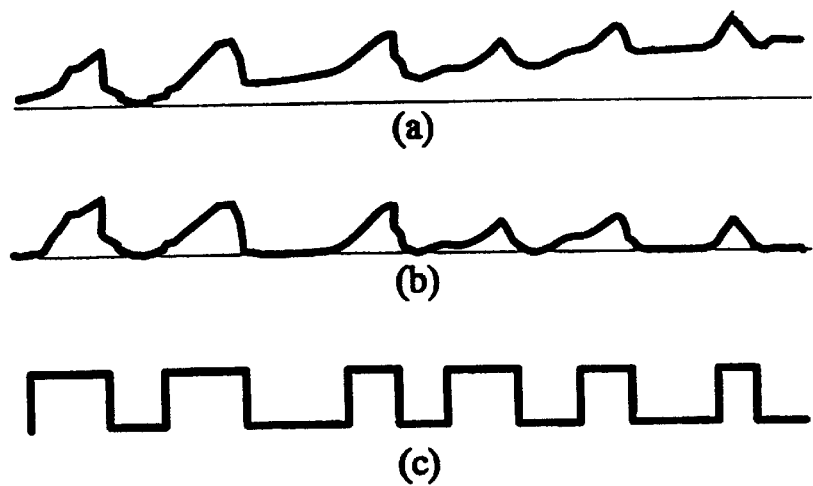
FIG. 4 illustrates exemplary array sums of a radiographic projection, from which the locations of knots can be calculated.

In the processing of log data, calculation time is saved by focusing exclusively on those parts of the log that contain knots or other anomalies. From the radiation received by the detector array 8, array sums are calculated, from which the positions of knots can be determined: since knots cause a greater attenuation than normal wood, the array sum for an image array containing knots is greater than for an adjacent array containing no knots. According to the invention, the aim is to locate those parts of the log which produce an increased array sum, which may contain knots. FIG. 4 presents an example of the variations of the array sums in the longitudinal direction of the log. In graph (a), the positions of knot clusters and also the log thickness are clearly visible.

Figure 5:
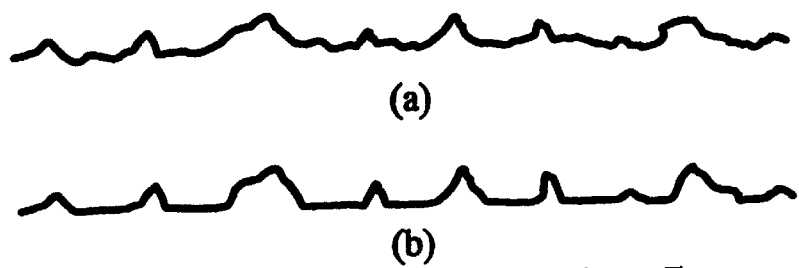
FIG. 5 represents the principle of filtering out the effect of stemwood from a radiographic projection.

In graph (b), the variation of log thickness has been filtered out. By performing median filtering on the start and end coordinates of the knot clusters, graph (c) is obtained. After the positions of knot clusters have been determined, the effect of stemwood is filtered out from the radiographic projections, so that only changes caused by knots and other anomalies remain. FIG. 5 presents a longitudinal section of a log without stemwood filtering (a) and another graph representing the same section with the effect of stemwood filtered out (b). The graph represents a longitudinal stripe of the log as seen by one detector element. In other words, this is a vertical stripe picked from a two-dimensional image. The log images contain a sufficient number of such stripes side by side.

Eligible filtering methods include e.g. average or median filtering. The filtering is performed by observing a series of points p(i) consisting of N measuring points, i.e. index (i) is assigned values 1 . . . N. The filtering compensates local variations, thus permitting larger entities to appear more clearly. In the case of the present invention, the filtering is performed to eliminate the effect of stemwood from the image, so what remains is the image produced by knots and other anomalies.

In average filtering, a new value q(i) is calculated for each point as follows:

$$q(i) = \sum_{j=i-m}^{i+m} p(j)/(2m+1)$$

To calculate a filtered value for a point i, an average is determined by considering m points on both sides of the point i. The number m is so selected that the variations to be filtered cover a length shorter than m points.

Correspondingly, in median filtering, points p(i−m)−p(i+m) are similarly considered to calculate a filtered value for points i. The numeric values of the points are ordered in sequence according to magnitude and the middle one is selected, called the median of this number series. Median filtering involves more computing work than average filtering, but it is not sensitive to the effects of individual large anomalies.

Figure 6:
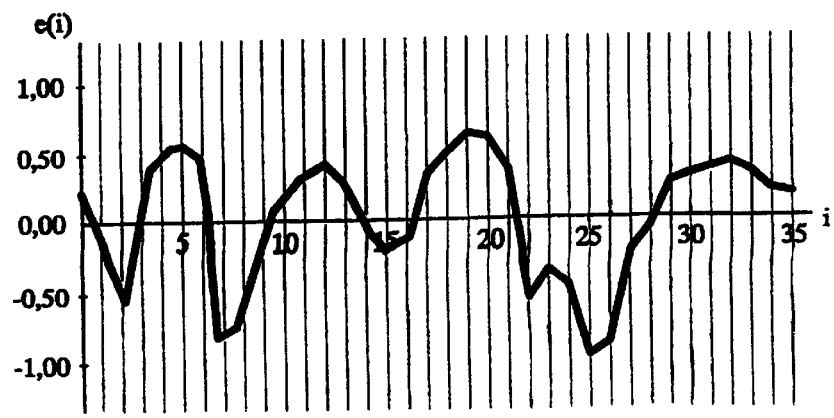
FIG. 6 illustrates an exemplary evidence graph for volumetric elements by sectors.

After the effect of stemwood portions has been filtered out from the radiographic projections, each knot cluster is processed separately as follows:

a) The three filtered radiographic projections are projected back to a system of 3-D coordinates by making use of back projection coefficients calculated beforehand. The coefficients take the known geometric properties of knots and trunk into account. This process divides the knot mass into volumetric elements.

b) The value of each volumetric element is indicative of the density of the wood in the element. Using experimental parameters, the density values can be converted into evidence values, which give a probability as to whether the volumetric element is part of a knot.

c) By combining the evidences of individual volumetric elements, truth values indicating possible knot sectors are obtained. FIG. 6 shows an example of a graph representing the truth values of log sectors. It can be seen from the graph that sectors 5, 12, 19 and 32 may contain knots.

d) Back projection as described under item a) is repeated, but this time only for selected rotational angles. In this way, side projections of the knots are obtained. From these projections, approximate upward gradient and spread angle values are now calculated.

Figures 7, 8:
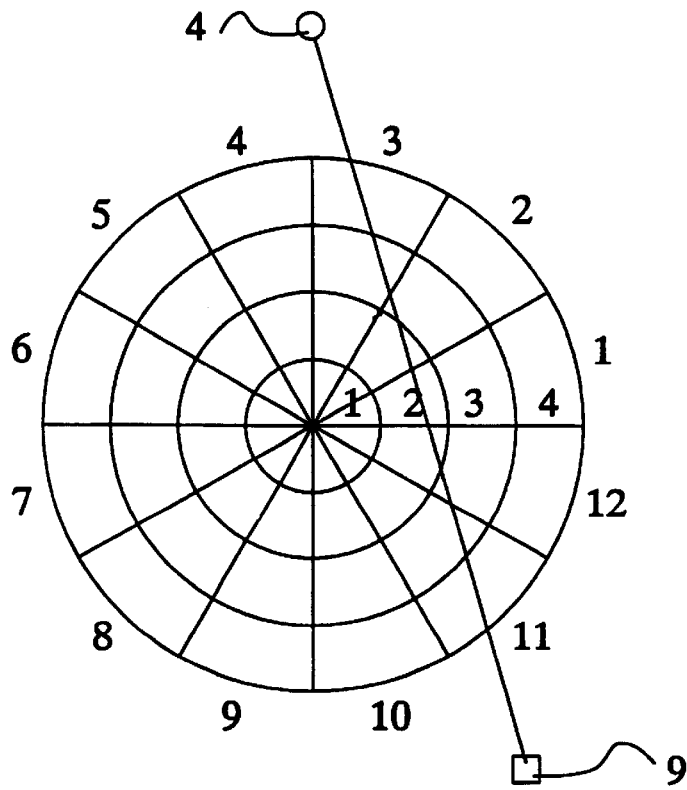
FIG. 7 describes a simplified illustration of the passage of an X-ray through a log divided into sectors and circles.
FIG. 8 presents a table of measurement results obtained in the case illustrated by FIG. 7.

The back projection and associated coefficients will be now described by referring to FIG. 7 and 8. The basic idea of the method of the invention derives from the fact that a knot starts from the core of the trunk and grows regularly expanding towards the trunk surface. Therefore, the calculation is advantageously performed using cylindric coordinates because the shape of a knot resembles a sector. FIG. 7 shows only 12 sectors to simplify the matter, whereas the system actually uses more sectors. Since the average knot width is 20°, a knot may occupy a space extending across two or three sectors. In the calculation, each radiographic projection is first processed separately. The measurement results are then processed to eliminate the effect of stemwood, leaving only the values representing knots. Other anomalies are not considered at this point in this description.

In FIG. 7, the sectors are numbered 1 . . . 12 and the circles 1 . . . 4. The figure shows one ray, which is emitted by the X-radiation source 4 and received by one 9 of the detector elements of a detector array. In the table in FIG. 8, the corresponding detector element is defined as pixel h. It is assumed that the ray has been attenuated during its passage through the log by an amount corresponding to ten units of knot mass, i.e. p(h)=10. The attenuation caused by a unit of knot mass has been determined experimentally beforehand, as stated before. However, a single measurement as described above is not sufficient to indicate where the knot is or whether there is only one knot or several knots. Still, it follows from the measurement geometry that only certain elements of the cross-section are to be considered. From FIG. 7 it can be seen that the ray passes through elements (1,2), (2,2), (2,3), (3,3), (3,4), (11,3), (11,4), (12,2) and (12,3). The first number in the element coordinates indicates the sector while the second number indicates the circle. Thus, the attenuation information received at pixel h can only come from these elements, from one or more of them.

As the contribution of each element to the attenuation obtained as a measurement result is not yet known at this point, it is assumed that the attenuation is evenly distributed throughout the passage of the ray in the log. In the case of our example, the distance travelled by the ray in the log is 73.50 mm. The measured ten units of knot mass is now divided among the above-mentioned elements in proportion to the distances travelled by the ray in each element. For example, the back projection coefficient for element (1,2) is the distance of ray travel in element (1,2) divided by the total travelling distance of the ray in the log, i.e. 8.50mm/73.50mm=0.12. As the attenuation value was 10, the projection result obtained for element (1,2) will be 10*0.12=1.2 (FIG. 8 shows a more precise reading). The coefficients c(h,i,j) used for the division have been calculated in advance and placed in a table as shown in FIG. 8 as explained above.

A complete table naturally contains the coefficients for all pixel, sector and circle values h, i and j. Most of the coefficients have a zero value because each ray only passes through a few elements.

The term 'back projection' here means that each radiographic projection is returned via computation to the two-dimensional section from which it was produced. In the table in FIG. 8, back projection has been performed with only one radiographic projection and only one detector element (pixel h). When the calculation is performed with all the radiographic projections and detector elements, i.e. with all the values obtained, and the results are summed for each element, then for each sector element a numeric value describing the knot mass contained in it will be obtained. If a high numeric value is obtained, then the element is likely to be part of a knot. When several high numeric values fall within the same sector, this further corroborates the notion that the sector contains knot mass. The numeric values are combined via a method called evidential inference. When the evidence or truth value for a sector exceeds a certain predefined threshold, the sector is accepted as a knot sector.

Because a large proportion of the knot mass obtained via the first back projection process seems to be spread even into sectors having no knots, the back projection process has to be repeated. This time, all sectors that are not regarded as knot sectors are omitted by setting their coefficients c(h,i,j) to zero. In this way, the knot mass can be placed exclusively in actual knot sectors.

As stated above, the size and direction of individual knots can be characterized in terms of radial length r and angles α, β and γ. These parameters can be used to calculate the assumed positions and areas of knots on the sawn surface. This makes it possible to obtain an advance estimate of the value of the log as timber, and in further processes even to optimize the sawing position on the basis of the knot data.

It is obvious to a person skilled in the art that the invention is not limited to the example described above, but that different embodiments of the invention can be varied within the scope of the following claims.

What is claimed is:

1. A method for determining the properties of a moving object constituted by at least a log, in which the moving object is radiographed by means of more than one radiation source emitting radiation capable of penetrating matter, and radiographic information therefrom is received by means of more than one detector measuring radiation capable of penetrating matter, wherein the method involves using knowledge relating to a known geometry, density and other properties constituting at least stemwood, knots and anomalies associated with the knots of the moving object, as well as to interdependencies between said properties, to allow sorting according to quality, wherein the radiographic information is analyzed to locate objects and parts of objects having the shape of a knot or other anomalies, which differ from the non-object containing material of the object being inspected, and wherein the effect of stemwood on the analysis is eliminated from the radiographic information via average or median filtering.

2. The method of claim 1, further comprising:

processing measured data by using pixel-specific attenuation information obtained via a radiographic projection from each radiation direction;

determining differences in attenuation between portions of wood material containing no objects and portions within the wood material containing objects;

comparing the attenuation differences both in a plane transverse to the log and in a known direction of growth;

identifying divergences obtained from the attenuation differences as positive and negative divergences based on logical inference rules;

identifying objects detected in the wood and verifying their location by using other measuring directions; and calculating the presence of objects in the wood material of the log based on a knowledge of known geometry and density of stemwood and knots in the log.

3. The method of claim 2, wherein a knot mass is converted from the radiographic projections to a plurality of volumetric elements in a system of cylindrical coordinates, wherein, from the value of each volumetric element, an evidence value representative of the presence of a knot in the element is derived, wherein the evidence values of mutually associated elements are combined to produce an evidence value for the aggregate, and, wherein directions of the knots are determined according to the highest total evidence values.

4. A method of analyzing a log to determine the presence of objects constituting at least stemwood and knots inside the log, comprising:

radiographing the log from at least one direction with at least one radiation source which penetrates the log therethrough;

obtaining measurement data from said radiographed log via at least one detector;

determining differences in radiation attenuation between a portion of the log having no objects therein and a portion containing objects, from pixel-specific attenuation obtained via a radiographic projection from said at least one direction;

determining positive and negative divergences in attenuation differences;
and
calculating the presence of a knot mass in the log based on a knowledge of known geometry and density of knots and stemwood, wherein the effects of stemwood on the calculation are removed due to the elimination of stemwood effects from said at least one radiographic projection by average or median filtering.

5. The method of claim 4, wherein the attenuation differences are compared in a plane which is transverse to the log as well as to a known direction of growth in the log.

6. The method of claim 4,
wherein said radiographing is performed by three radiation sources equally spaced from one another in circumferential relation to the log, each providing a plurality of radiographic projections representing a possible knot mass which are detected by corresponding detectors of a detector array, and
wherein the presence and approximate location of knots and stemwood in the log are initially identified by information from said plurality of radiographic projections.

7. The method of claim 6,
wherein said plurality of radiographic projections representing a possible knot mass are converted into volumetric elements of a cylindrical coordinate system, each volumetric element assigned a truth value which, when combined, provide information to calculate the direction of knots in said log; and
wherein array sums are calculated from said detector array to determine positions of knots in said log.

8. A method of analyzing a log to determine the presence of objects constituting at least stemwood and knots inside the log, comprising:
radiographing the log with three equally spaced radiation sources to provide three radiographic projections which contain X-ray attenuation data;
performing average or median filtering to eliminate the effects of stemwood from an image of the object resulting from said three radiographic projections;
re-projecting said three filtered radiographic projections onto a 3-D cylindrical coordinate system by using predetermined coefficients to divide the object into volumetric elements, each element indicative of a density value of the object;
converting the density values into evidence values which give a probability as to whether a volumetric element is part of a knot; and
combining the evidence values to form an aggregate evidence value for a sector, wherein the direction, size and location of the object is determined in accordance with the sector having the largest evidence values.

9. The method of claim 8, further comprising
identifying an initial presence of a possible object in the log from the attenuation data,
wherein the radiographic projections are converted into volumetric elements representative of a 3-D cylindrical coordinate system, and
wherein truth values are assigned to each volumetric element and combined to obtain a truth value for a sector of the object; and
determining an initial approximate position of the object from the calculation of array sums from the radiation received by a detector array, wherein said steps of identifying and determining are performed prior to said step of filtering to provide an initial estimate of the presence and location of the object in a log.

10. The method of claim 8,
wherein said attenuation data is used to determine attenuation differences between portions of the log which contain no objects, and portions of the log containing the object; and
wherein said attenuation differences are compared in a direction which is transverse to both the log and to a known direction of growth of the log.

11. The method of claim 10, wherein divergences obtained from the attenuation differences are identified via the use of logical inference rules.

* * * * *